United States Patent [19]

Medero

[11] Patent Number: 4,546,775
[45] Date of Patent: Oct. 15, 1985

[54] DETECTION OF BLOOD PRESSURE COMPLEXES IN AUTOMATED VITAL SIGNS MONITORS

[75] Inventor: Richard Medero, Lutz, Fla.

[73] Assignee: Critikon, Inc., Tampa, Fla.

[21] Appl. No.: 621,647

[22] Filed: Jun. 18, 1984

[51] Int. Cl.[4] ................................................ A61B 5/02
[52] U.S. Cl. .................................... 128/681; 128/680
[58] Field of Search ......................... 128/677, 680–683

[56] References Cited

U.S. PATENT DOCUMENTS

| | | | |
|---|---|---|---|
| 3,903,872 | 9/1975 | Link | 128/681 |
| 4,009,709 | 3/1977 | Link | 128/681 |
| 4,074,711 | 2/1978 | Link | 128/681 |
| 4,105,021 | 8/1978 | Williams et al. | 128/683 |
| 4,154,238 | 5/1979 | Link | 128/681 |
| 4,174,707 | 11/1979 | Link | 128/681 |
| 4,271,843 | 6/1981 | Flynn | 128/681 |
| 4,325,382 | 4/1982 | Miodownik | 128/673 |
| 4,328,810 | 5/1982 | Hill et al. | 128/682 X |
| 4,349,034 | 9/1982 | Ramsey | 128/681 |
| 4,360,029 | 11/1982 | Ramsey | 128/681 |
| 4,367,751 | 1/1983 | Link | 128/682 |
| 4,408,614 | 10/1983 | Weaver et al. | 128/680 |
| 4,461,266 | 7/1984 | Hood, Jr. et al. | 128/677 X |

OTHER PUBLICATIONS

Ramsey; "Noninvasive Automatic Determ. of Mean Arterial Press.,"; Med. and Biol. Engr.; 1-1979, vol. 17, No. 1, pp. 11-18.
Looney; "Blood Press. by Oscillometry"; Med. Electronics, 4-1978, pp. 57-64.

Primary Examiner—Lee S. Cohen
Assistant Examiner—Angela D. Sykes
Attorney, Agent, or Firm—Audley A. Ciamporcero, Jr.

[57] ABSTRACT

A blood pressure cuff is applied to the patient, pumped to a pressure above systolic, and then is reduced in pressure decrements. At each decrement, complexes are detected by investigating the signal slope, and peaks of the complexes are measured and compared. During the complex detection process, the signal slope is measured periodically at a rapid rate, and unless the slope meets predetermined criteria, the input filters are clamped to a baseline, and the process is repeated.

7 Claims, 3 Drawing Figures

DETECTION OF BLOOD PRESSURE COMPLEXES IN AUTOMATED VITAL SIGNS MONITORS

FIELD OF THE INVENTION

This invention relates to automated vital signs monitoring, and more particularly to improved techniques for automated blood pressure monitoring.

BACKGROUND OF THE INVENTION

Automated blood pressure monitoring has rapidly become an accepted and, in many cases, essential aspect of human and veterinary treatment. Such monitors are now a conventional part of the patient environment in emergency rooms, intensive and critical care units, and in the operating theatre.

The so-called oscillometric method of measuring blood pressure is one of the most popular methods in commercially available systems. This method relies on measuring changes in arterial counterpressure, such as imposed by an inflatable cuff, which is controllably relaxed. In some cases the cuff bleed is continuous, and in others it is incremental, but in substantially all, a transducer monitors arterial counterpressure oscillations, and processing apparatus converts select parameters of these oscillations into blood pressure data. The units available from the assignee hereof under the trade name DINAMAP* Vital Signs Monitor provide an excellent example of automated blood pressure monitors employing the oscillometric methodology.

A prime aspect of accurate automated monitoring is the discrimination of true counterpressure data from artifact data. Such artifact data may result from physiological events such as patient movement or shock to the cuff through external contact, or may result from internally generated artifacts, such as noise or other effects produced by system componentry.

One class of artifact rejection techniques is exemplified by those taught in U.S. Pat. Nos. 4,349,034 and 4,360,029 to M. Ramsey, III, commonly assigned herewith. The Ramsey patents disclose an incremental deflation apparatus wherein, at each pressure level, plural counterpressure oscillatory complexes produced by heartbeats (referred to herein simply as "complexes") are detected, and select parameters such as peak height and time rate of change of successive samples and successive series of samples are evaluated relative to specified artifact discrimination criteria. See also U.S. Pat. Nos. 3,903,872; 4,009,709; 4,074,711; 4,154,238; 4,174,707; 4,367,751 to Link.

It will be apparent, then, that even those systems employing very elaborate artifact rejection algorithms to process the parameters of the oscillatory complexes are subject to error if the complexes themselves are inadequately or inaccurately sensed in the first instance. In particular, it is noted that the counterpressure complexes constitute relatively low level, noisy signals superimposed on the much larger, sometimes poorly regulated cuff pressure baseline. Accordingly, it is conventional first to subject the signals to band pass filters which tend to pass the complex but to block noise on the high frequency end, and the base cuff pressure and slower variations thereof at the low end. It has been found, however, that this very filtering, and particularly the high pass sections thereof, can contribute inaccuracy to the complex detection and measurement process. In such a filter, which can be simply modeled as a single section RC high pass network, the input coupling capacitor acts as a memory element. That is, signals in the near or distant past have some effect on signals generated at any time, based upon the amplitude of such signals (which proportionally add charge to the capacitor when they occur) and the RC time constant of the network (which establishes the rate of exponential discharge of the capacitor). Accordingly, it is possible at any given time for the actual counterpressure signal, when applied to the high pass input filter, to be "combined" with remnants of prior signals as represented by instantaneous charge on the capacitor, and thus to be erroneously interpreted by subsequent processing circuitry.

It is an object of the present invention to eliminate the untoward effects on the complex detection process imposed by operation of input filtering componentry.

SUMMARY OF THE INVENTION

The principles of the present invention are premised upon frequent periodic monitoring of signals from input filters, and at each such determination, evaluating the likelihood that a "true complex" is being presented. In accordance with the present invention signal slope is deemed to be an indicator of prospective occurrence of a complex. If the slope of the signal is uncharacteristic of that at the initiation of a true complex, the output of the filter is clamped, the capacitor is discharged, and the process is repeated. In this fashion, the historical effect of signals at the input to the filter is eliminated except during the occurrence of a true complex, at which time the slope is within defined limits, and the periodic clamping process is not conducted. In other words, in operation, the filter is repeatedly reset (i.e., discharged) and the filter output is then observed for the presence of a signal characteristic of the pulsation to be measured. If the signal looks like a pulsation, the clamp is not reset and the pulsation is allowed to pass and be measured. If the signal does not have characteristics of a pulsation (e.g. wrong slope direction, or proper slope direction but wrong slope magnitude), the filter is clamped and the process repeated.

BEST MODE FOR CARRYING OUT THE INVENTION

Figure 1:
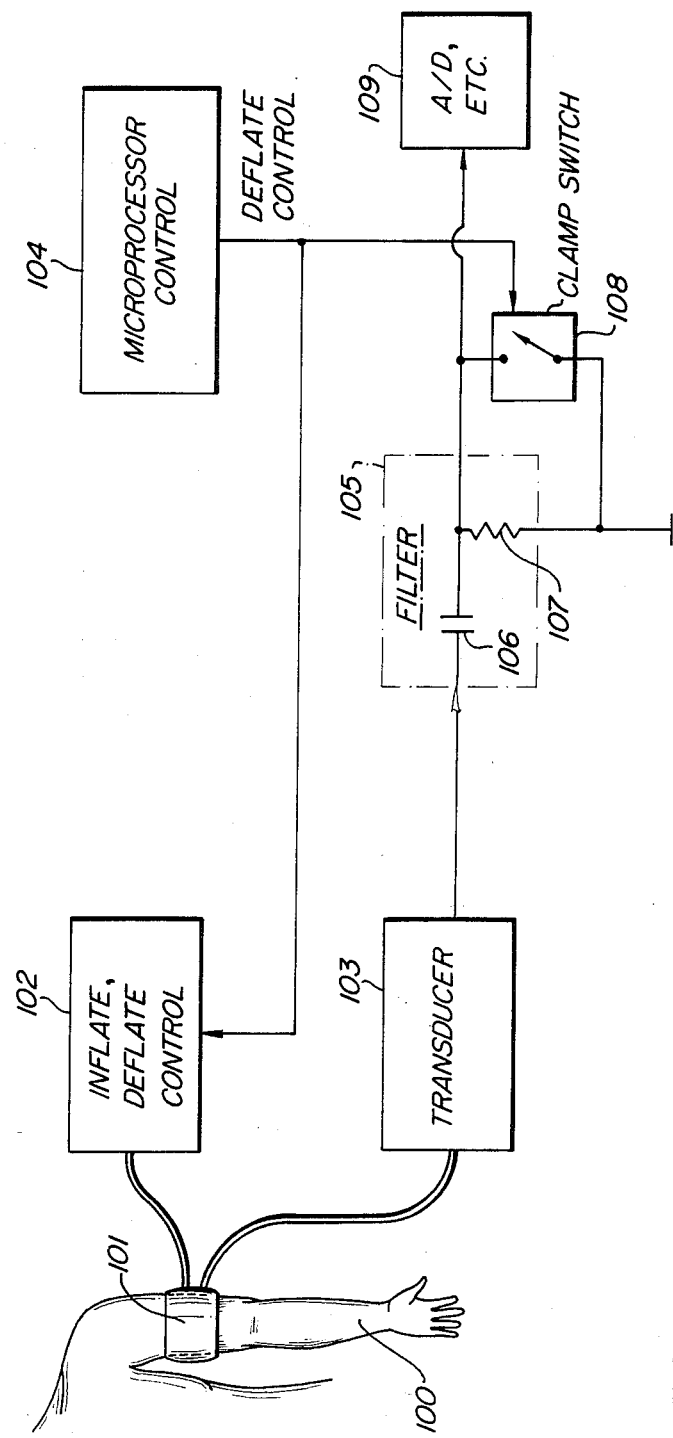
FIG. 1 shows a prior art approach to utilization of clamps for rejection of artifact data.

Referring first to FIG. 1, there is shown a prior art approach known to the inventor hereof which utilizes clamping for certain artifact rejection aspects of automated blood pressure monitoring. In particular, the FIG. 1 embodiment is representative of the operation of the DINAMAP* Model 845 blood pressure monitors and its predecessors, marketed by the assignee hereof prior to the present invention. The FIG. 1 apparatus is directed to avoidance of artifacts generated at times during which the pressure cuff is decremented from pressure level to pressure level. In particular, the FIG. 1 apparatus addresses the recognition that each such pressure decrementation will place some charge on the coupling capacitor of a high pass input filter, and that such residual charge on the capacitor will, at the next pressure level, distort the accuracy of the complex detection process for a certain time. Accordingly, the apparatus of FIG. 1 operates to clamp the filter output during such times as the cuff pressure is being decremented.

In FIG. 1, a cuff 101 is shown suitably disposed on the arm 100 of the patient, such as over the brachial artery. The cuff pressure is established and regulated by a control unit 102, which in conventional fashion includes pumps and valves to control pressure in the cuff 101. Also in conventional fashion, cuff pressure, and the inflation and deflation process, proceeds under control of a microprocessor 104. As shown in FIG. 1, a separate control line couples the microprocessor 104 to a deflation or bleed valve (not specifically shown) in the pressure control unit 102. Thus, for example, depending upon the overall system operation, the microprocessor 104 will periodically cause the pressure in cuff 101 to be reduced (either in increments during the measurement process, or totally at the end of the measurement process) through application of control signals on the deflate control line. In practice, this may be achieved as simply as by transmitting a control pulse on the deflate control line which energizes a solenoid on the deflate valve for the duration of the pulse.

Pressure in the cuff is sensed by a transducer 103, which converts pressure to electrical signals, which in turn are coupled to filtering means 105. It is to be understood that filters in actual practice may be quite complex, and may entail both high pass and low pass sections. Further, the high pass sections thereof may be quite complex, depending upon the precise signal attenuation characteristics desired in the various frequency bands. In accordance with the precepts of network theory, however, and certainly adequately for purposes of discussion herein, the high pass aspects of input filters may be modeled as a simple RC section, with an input or coupling capacitor 106 followed by a resistor 107 to ground or other suitable baseline. The output of the filter 105 is therefore expressed as the voltage across the resistor 107. In conventional fashion, the filter 105 has an exponentially decreasing gain (i.e. attenuation) with a time constant equal to the product of the capacitance C of capacitor 106 and the resistance R of the resistor 107. That is, $V_{out}(t) = V_{in}(t)e^{-t/RC}$.

Therefore, the baseline and slowly changing (i.e. low frequency) aspects of the signal from transducer 103 are blocked by the filter 105, whereas the more rapidly changing (i.e. high frequency) components are passed to the balance of the signal processing circuitry, which in FIG. 1 is simply aggregated in the block 109.

In FIG. 1, a clamp switch 108 bridges the resistor 107 of filter 105, and operates in conjunction with the deflation control signal from the microprocessor 104. Normally, the clamp switch 108 is open. During times of deflation of the cuff, however, the same signal which causes the deflate valve at 102 to operate, also closes the clamp switch 108. When the deflation has been completed, the clamp switch 108 is opened, and the normal filtering operation is conducted. Thus, in the FIG. 1 prior art embodiment, it will be seen that the clamp 108 maintains a specified baseline during times of deflation, and hence avoids having those signals provide a bias offset or other lingering effect which would cause inaccuracy of complex detection at the next subsequent pressure level.

The FIG. 1 system is adequate, therefore, to eliminate by use of clamping certain filter induced artifacts. Being quite limited in scope, however, the FIG. 1 system fails to address a number of other filter induced artifacts, which are addressed in accordance with the principles of the present invention. In particular, in practice, the instrument has no a priori knowledge of exactly when a pulsation is about to occur, and hence when a complex is about to occur. Thus, while the FIG. 1 type system utilizes clamping effectively to obviate artifacts arising from the known condition, that is cuff deflation, it provides no basis for avoiding unanticipated filter induced artifacts at other times and for other artifact conditions. By addressing these other times and other conditions, the principles of the present invention provide a more active, "closed loop" control for the clamp in a quasi-continuous discrimination of filter induced artifacts. The term quasi-continuous is used here because, although in preferred embodiments the sensing is not absolutely continuous (although theoretically it may be), it is in all events conducted periodically at a high rate of repetition such that a high percentage of such artifacts will be sensed, and true complexes will not be missed.

Figure 2:
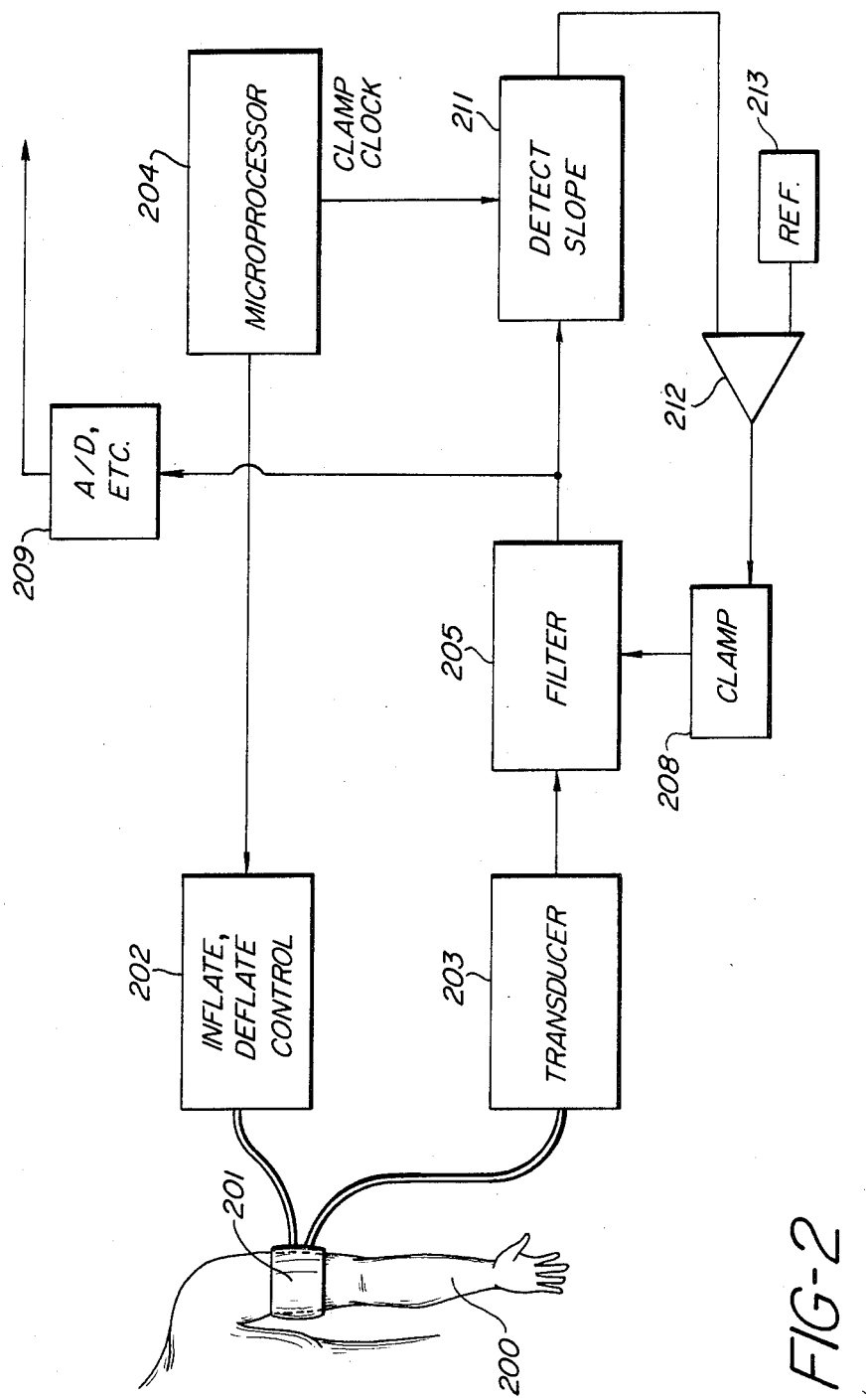
FIG. 2 is a schematic diagram of a system employing the principles of the present invention.

Referring, then, to FIG. 2, there is shown a schematic diagram of an illustrative embodiment of the principles of the present invention. In salient respects, the FIG. 2 embodiment is configured identically to that of the FIG. 1 prior art system, save for those aspects relating to the principles of the present invention. Thus, pressure in the cuff 201 is established by an inflation—deflation control unit 202, which in turn operates under control of the microprocessor 204. Inasmuch as the operation of the FIG. 2 system is not slavishly dependent on deflation control signals, but a single interconnection is shown between microprocessor 204 and pressure control 202, it being understood that such connection may indeed reflect multiple control functions.

The pressure in the cuff 201 is sensed by a transducer 203, which passes such signals on to a filter 205. It is understood that the filter 205 may in its high pass aspects be modeled as a single section RC filter as shown in FIG. 1, but that it may well be more complex in fact. From the standpoint of the principles of the present invention, however, the filter 205 operates in conjunction with a clamp 208 (in its simplest form, a switch appropriately located and controlled, as in FIG. 1) in the same fashion as did the clamp 108 in FIG. 1. As will be shown, however, the salient aspects of the principles of the present invention rather relate to apparatus, logic, and methodology for control of the clamp.

Figure 3:
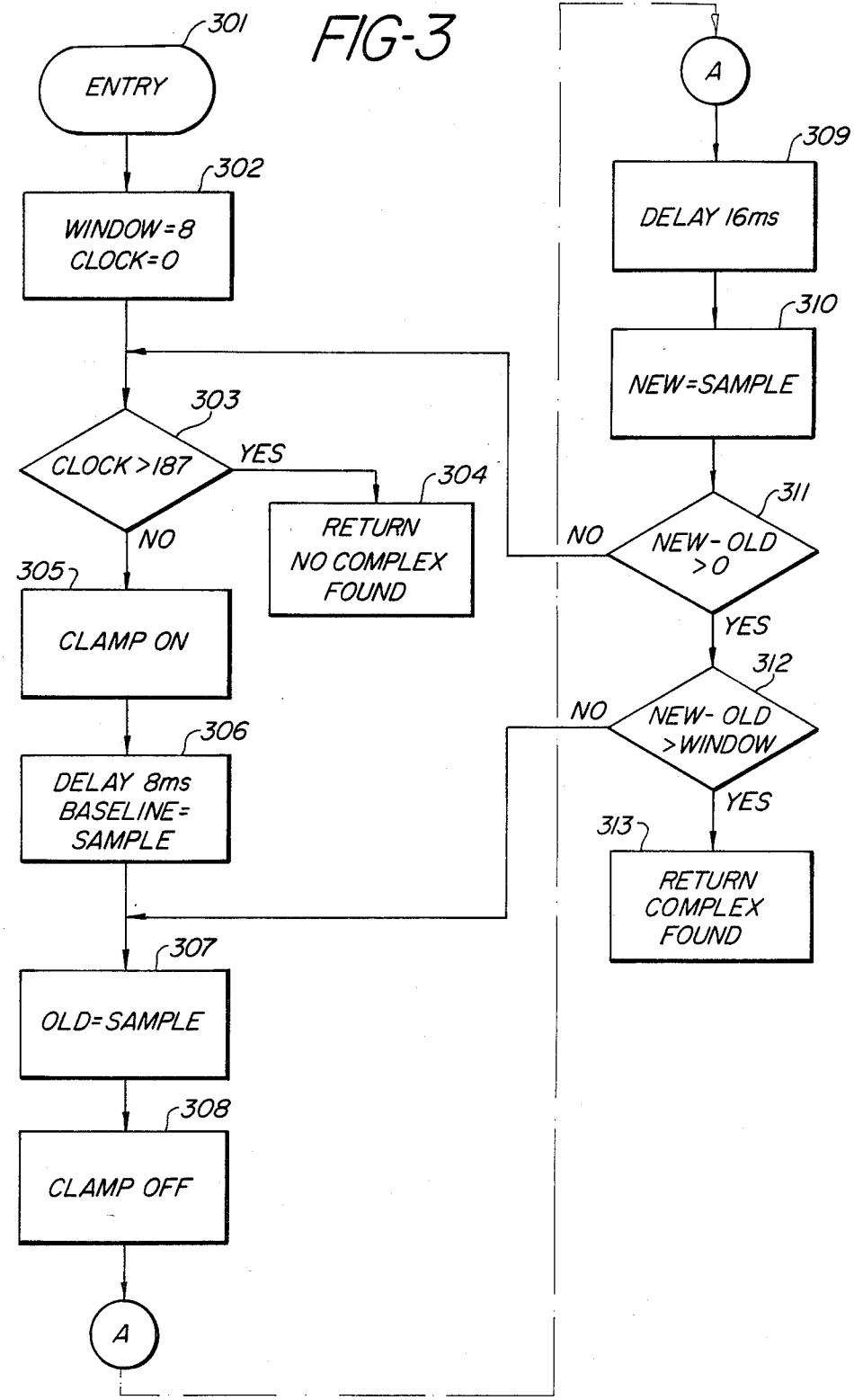
FIG. 3 shows a flow chart of methods embodying the principles of the present invention.

In this respect, it will be noted that FIG. 2 shows clamp control in accordance with the principles of the present invention as a traditional, hard wired system wherein the microprocessor 204 has minimal active control functions (i.e. essentially only clocking). FIG. 3 shows a flow chart format for a software embodiment, which it is understood would be executed by the microprocessor and which would obviate comparable hard wired apparatus as shown in FIG. 2.

In FIG. 2, as in FIG. 1, the main signal flow is from the transducer 203 to the filter 205 to the balance of the unit, designated in FIG. 2 as block 209. The output signal from the filter is also coupled to a slope detection block 211, which is shown to be energized by clock signals from the microprocessor 204. It will be appreciated that differentiation attendant to slope detection may well be an inherent characteristic of the filter 205, but for clarity and in the general case, the slope detection is shown in FIG. 2 as a discrete function at block 211. In analog embodiments, slope detection will be recognized as a simple differentiation function, and a similar result may be obtained on a digital basis by determining the amplitude change between successive discrete samples separated by a known time differential.

The so-called "clamp clock" from the microprocessor 204 enables the slope of the filter output signal to be evaluated by the slope detection network 211 at a specific periodicity and for a specific time, both of which are much smaller than the rate of change or occurrence of complexes (e.g. evaluating the slope for a duration of 16 milliseconds once every 24 milliseconds). The slope as so detected is coupled to a comparator 212, where it is compared to reference 213. In the normal course, true complex signals will have a substantial positive going slope, above that represented by the reference 213. Thus, in FIG. 2, if the slope as detected at 211 and coupled to the comparator 212, is greater then the reference, the clamp switch 208 remains open and the true complex signal so detected is passed from the filter 205 to the balance of the circuitry 209. If, however, the slope is less than the reference (i.e. it is negative going in slope, or is positive going but of an amplitude less than the reference), the clamp switch 208 is caused to be closed, the filter output is clamped to the baseline, and the associated input data is not advanced through the filter 205 to the balance of the circuitry. The clamp remains closed for a specified period of time, is opened well before the next sample is to be evaluated (i.e., before the next clamp clock pulse) and the process continues.

The procedure exemplified by the embodiment of FIG. 2 may perhaps be better understood upon consideration of FIG. 3, which shows the process in flow chart form. Further, the flow chart embodiment of FIG. 3 is well adapted to be coded into a computer software routine, resident for example in the microprocessor 204, directly to control the operation of the clamp 208.

Entry to the routine is specified at 301, and at step 302 a pair of variables designated "WINDOW" and "CLOCK" are set, the former to the number 8 and the latter to the number 0. The "WINDOW" variable corresponds to the comparison reference 213, that is, to the comparison threshold against which clamp operation is established. The "CLOCK" variable is an external time accrual variable, incremented by the system clock. At the completion of a predetermined number of clock cycles, it may be concluded that no complexes are to be found, and the procedure is to be recycled, for example at a new pressure level.

In fact, at the next step, decision 303, a test is made whether the "CLOCK" variable is greater than 187 (i.e., the predetermined number of iterations just referred to). If so, no complex is deemed found at the pressure level in question, the "yes" branch is followed, and at return step 304 the FIG. 3 processs exits. If the "CLOCK" variable is less than 187, the search for a complex is still on, the "no" branch is followed, and at 305 the clamp is energized (i.e. the switch is closed). In the first instance, this establishes a baseline; in later instances baseline is restored in accordance with the principles of the present inviention. At 306, the system clamps by delaying for a predetermined amount (e.g. 8 milliseconds, and a "baseline" variable is set to be the value of the sample (i.e. the filter output) at that time.

Next, at 307, a first reference variable "OLD" is set also to be the sample value. Then, at 309, the clamp is disabled (i.e. the switch is opened). The OLD variable is the first of two which establish an amplitude change for calculation of slope.

After a 16 millisecond delay, a new sample is taken, which sample value is assigned to the variable "NEW". Next, at 311, the difference between "NEW" and "OLD", which in fact is the amplitude difference between successive samples, and hence represents the change in amplitude over the 16 millisecond delay (i.e. the slope) is evaluated at 311. If this difference is not greater than zero, the "no" exit is taken. If the difference between the variables NEW and OLD is greater than zero, the "yes" branch is taken from 311, and at 312 the difference is compared to the "WINDOW" variable. If the NEW to OLD difference is larger than the "WINDOW" variable, a complex has been found, the "yes" branch is taken, and at 313 the procedure is exited for further processing. If not, the "no" branch is taken, in this instance back to point 307, where the sample value which had been NEW is assigned to the variable "OLD". In this case, clamping is not done because the positive going slope, albeit less than the window, suggests the possibility of initiation of a complex. Thus, the repetition of steps 309, 310, 311, and so forth is commenced, but simply going on to the next sample.

It will be appreciated that the foregoing procedure is readily amenable to coding in a suitable language, for example assembly language which operates in conjunction with the particular model of microprocessor being used. In such embodiments, the microprocessor will directly control the operation of the clamp switch. It will also be appreciated, however, that the procedure and methodology of FIG. 3 provides ample basis for the design of hard wired circuits which employ the same logic. Such circuits may, for example, be utilized in systems such as described in the foregoing Ramsey et al. patents.

To the extent required to complete the disclosure hereof, the Ramsey patents are incorporated by reference herein. Likewise, to the extent required to complete the disclosure herein, the manuals provided in conjunction with the DINAMAP* Model 1846 vital signs monitors, in which the present invention is embodied in software form, is incorporated by reference herein.

It is to be noted that the illustrative embodiments described herein, both in apparatus and method terms, relate to the active, periodic control of a clamping operation for correction of filter induced artifacts in high pass filters. It will be appreciated that the same rationale may be gainfully applied to other filtering sections in which artifacts are induced through the charge storage functions of capacitors. These and other variants will occur to those of ordinary skill in the art based on the spirit and scope of the principles of the present invention, and based on the disclosures provided herein.

I claim:

1. An oscillometric blood pressure monitor comprising:
   (a) means for sensing arterial pressure pulsations;
   (b) transducer means, responsive to said means for sensing, for producing signals representative of said pulsations;
   (c) means, responsive to said transducer means, for filtering said signals to pass at least signals of a frequency band corresponding to oscillatory complexes;

(d) means for selectively clamping the output of said means for filtering to a predetermined baseline; and (e) control means, responsive to the slope of said signals from said means for filtering, for enabling said means for clamping.

2. A monitor as described in claim 1 wherein said control means comprises means for comparing slope of said signals with a reference, and means for enabling said means for clamping unless said slope is greater than said reference.

3. A monitor as described in claim 2 wherein said means for comparing operates periodically at a high rate compared to the rates of occurrence of arterial pressure pulsations.

4. A monitor as described in claim 2 wherein said reference corresponds to a predetermined positive slope characteristic of the onset of a blood pressure complex, and said control means enables said means for clamping upon occurrence of signals having negative slope or positive slope less than said reference.

5. A monitor as described in claim 1 wherein said means for sensing comprises an inflatable blood pressure cuff, said means for filtering includes a high pass section to eliminate components of said signals generated by any baseline and slow changes from said transducer means, and said means for clamping is operated to clamp said high pass section.

6. In an oscillometric blood pressure monitoring method of the type which processes arterial counterpressure oscillations into blood pressure data, an improved complex detection method comprising;

(a) periodically sensing the slope of counterpressure oscillations;

(b) comparing said slope with a reference; and (c) blocking further processing of the counterpressure oscillations for a predetermined time unless said slope is greater than a predetermined reference.

7. In an oscillometric blood pressure monitor of the type including means for transducing signals representative of blood pressure pulsations in a subject, and filter means for isolating the pulsatile components in said signals, and providing output signals corresponding thereto, the improvement comprising apparatus for avoiding select artifact data comprising:

(a) a source of timing signals;

(b) means, responsive to timing signals, for periodically evaluating the slope of signals from said filter means;

(c) means for selectively clamping the output of said filter means to a predetermined baseline; and (d) means for enabling said means for clamping when said slope is less than a predetermined amount.

* * * * *